United States Patent [19]

Goldman et al.

[11] Patent Number: 4,883,173
[45] Date of Patent: Nov. 28, 1989

[54] HYPODERMIC NEEDLE REMOVAL AND DISPOSAL DEVICE

[76] Inventors: Diana L. Goldman; Michael S. Goldman, both of 5109 Foxon Rd., Virginia Beach, Va. 23464

[21] Appl. No.: 359,577

[22] Filed: Jun. 1, 1989

[51] Int. Cl.$^4$ .............................................. B65D 25/00
[52] U.S. Cl. .................................. 206/366; 206/63.5; 206/370
[58] Field of Search ...................... 206/366, 63.5, 370, 206/380

[56] References Cited

U.S. PATENT DOCUMENTS

| | | |
|---|---|---|
| 3,876,067 | 4/1975 | Schwarz . |
| 4,027,669 | 6/1977 | Johnston et al. . |
| 4,351,434 | 9/1982 | Elisha . |
| 4,375,849 | 3/1983 | Hanifl . |
| 4,452,358 | 6/1984 | Simpson . |
| 4,466,538 | 8/1984 | Gianni . |
| 4,488,643 | 12/1984 | Pepper . |

*Primary Examiner*—Joseph Man-Fu Moy
*Attorney, Agent, or Firm*—Griffin, Branigan & Butler

[57] ABSTRACT

A hypodermic needle removal and disposal device (10) for removing hypodermic needle assemblies (62) from hypodermic syringes (60) comprises an elongated storage container (12) which can be held in one hand having at a top end thereof a needle removing shield (24). The needle removing shield includes an apron (26) for extending laterally outwardly beyond an outer surface (14) of the elongated storage container and a funnel-shaped top surface (30) slanting toward a cone shaped needle-removal plateau (28). The needle-removal plateau forms an elongated hole (44) through a plateau surface (46) thereof having a size that is only slightly larger than hubs (66) of hypodermic needle assemblies. Hypodermic syringes can be maneuvered so that needle assemblies mounted thereon extend into the elongated hole and the hypodermic syringe can then be rotated laterally about the hub of the hypodermic needle assembly. The hub is held stationary by the elongated hole and cannot follow this rotation, thus, threads which engage the hypodermic syringe with the hypodermic needle assembly are separated. The needle assembly falls into the elongated storage container.

11 Claims, 3 Drawing Sheets

HYPODERMIC NEEDLE REMOVAL AND DISPOSAL DEVICE

BACKGROUND OF THE INVENTION

The disposal of hypodermic needle syringes has been the subject of a great deal of interest in recent years because of the spread of various blood-transmitted diseases. In this respect, a number of medical personnel have been infected when they inadvertently stuck themselves with needles which had been used to treat infected patients.

A number of hypodermic needle disposal devices allow medical personnel to dispose of entire hypodermic syringes, including needle assemblies attached thereto. One such syringe and needle disposal system is described in U.S. Pat. No. 4,488,643 to Pepper. A difficulty with these systems is that some medical personnel use syringes which are not disposable. For example, dentists normally use surgical stainless steel metallic hypodermic syringe frames in which vials containing anesthetics are inserted. The anesthetics are dispensed through disposable plastic needle assemblies mounted on the stainless steel syringe frames. These metallic hypodermic syringe frames are not disposable. Thus, it is an object of this invention, to provide a hypodermic needle disposal device which allows one to remove a hypodermic needle assembly from a hypodermic needle syringe and then dispose of the needle assembly without endangering medical personnel.

Some hypodermic needle assembly disposal devices include pawl-like members which allow a hypodermic needle assembly hub to pass one-way through a hole, but which fall into place behind the needle assembly hub to not allow it to be removed from the hole. Several such systems are described in U.S. Pat. Nos. 3,876,067 to Schwarz and 4,351,434 to Elisha. Although it appears that these systems would work well for some hypodermic needle assembly arrangements, it is not thought that they would work well for those which are screwed onto spiral threads of hypodermic syringes because such pawl members usually do not retain the hypodermic needle assemblies from rotating when one unscrews the threads of the needle assemblies from the syringes. Thus, it is an object of this invention to provide a hypodermic needle removal and disposal device which allows medical personnel to quickly and efficiently remove a hypodermic needle assembly from a hypodermic syringe to which it is attached by spiral threads.

There are a number of hypodermic needle assembly removal devices having holes therein with teeth thereabout for gripping a hub of a hypodermic needle assembly to hold it still while a hypodermic syringe is screwed therefrom. Such arrangements are disclosed in U.S. Pat. Nos. 4,375,849 to Hanifl, 4,452,358 to Simpson, and 4,466,538 to Gianni. A difficulty encountered in using such devices is that it is awkward for medical personnel to rotate with one hand a syringe about its lengthwise axis for unscrewing its nozzle from a hub of a needle assembly. Thus, it is a further object of this invention to provide a hypodermic needle removal and disposal device with which a hypodermic needle assembly can be removed from a hypodermic syringe without rotating the syringe about its lengthwise axis.

It is also an object of this invention to provide a hypodermic needle removal and disposal device which is virtually completely safe and with which there is virtually no chance of an operator inadvertently puncturing himself or herself.

SUMMARY

According to principles of this invention, a hypodermic needle removal and disposal device includes an elongated storage container having a side wall which can be gripped by a normal-size human hand to be held in an upright attitude. A needle-removing shield permanently mounted on top of the elongated storage container has an apron extending laterally, outwardly, substantially beyond an outer surface of the side wall. The apron has a funnel-shaped top surface facing away from the storage container slanting downwardly toward an upstanding needle-removal plateau. The plateau rises above the funnel shaped top surface to form a plateau surface thereabove defining an elongated hole therein with a relatively uniform dimension along a length thereof. The elongated hole is sized to closely receive a hub of a disposable hypodermic needle.

To remove a plastic hypodermic needle assembly from a hypodermic syringe, the hypodermic syringe is manipulated so that a hypodermic needle assembly mounted thereon extends down into the elongated hole and the hypodermic syringe is then rotated laterally about the hub of the hypodermic needle assembly. The hub is prevented from rotating by a wall forming the elongated hole. Thus, spiral threads of a nozzle of the hypodermic syringe are ripped out of engagement with spiral threads of the hypodermic needle assembly hub.

BRIEF DESCRIPTION OF THE DRAWINGS

The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

DETAILED DESCRIPTION OF THE PREFERRED EMBODIMENT

Figure 1:
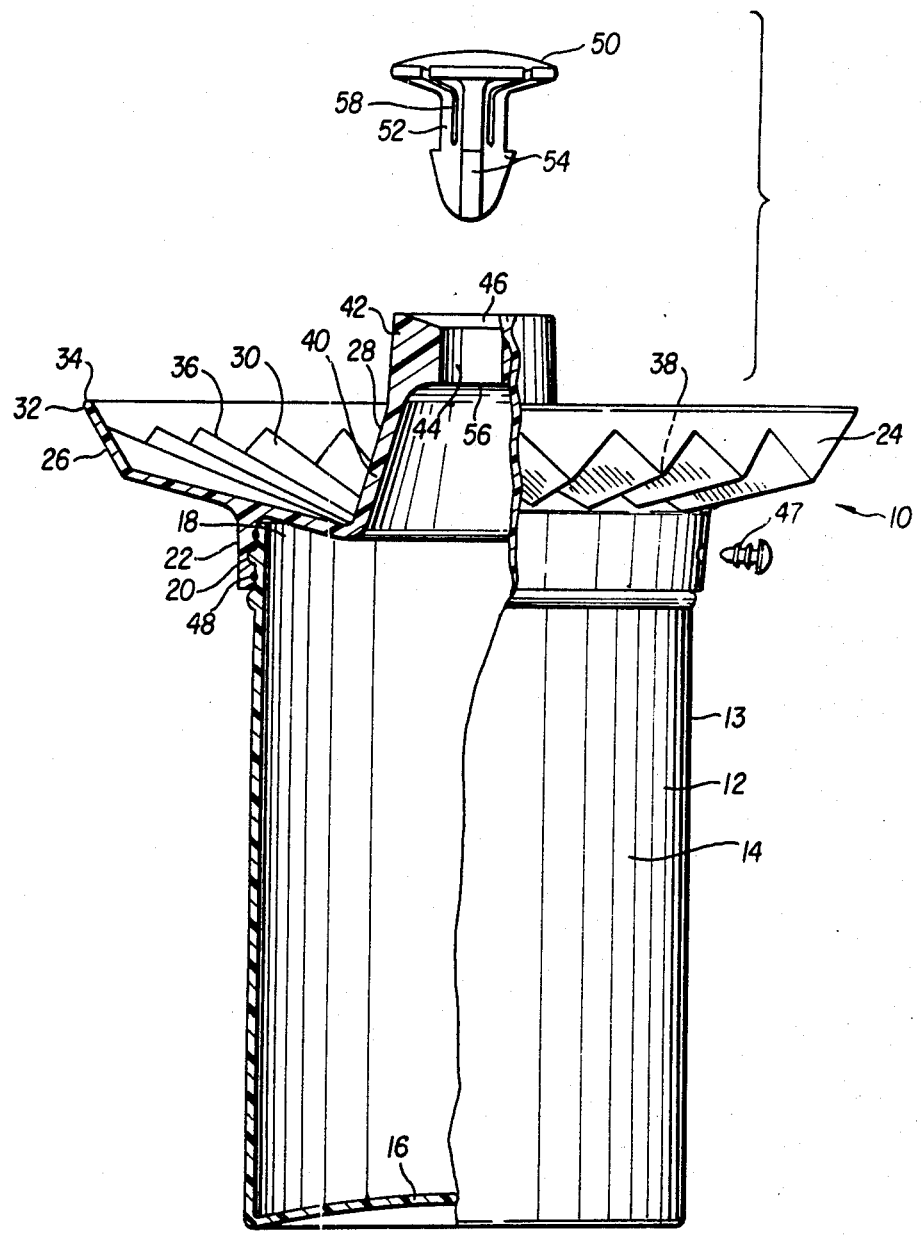
FIG. 1 is a side, exploded, partially cutaway, view of a hypodermic needle removal and disposal device of this invention including a covering cap exploded therefrom.
Figure 2:
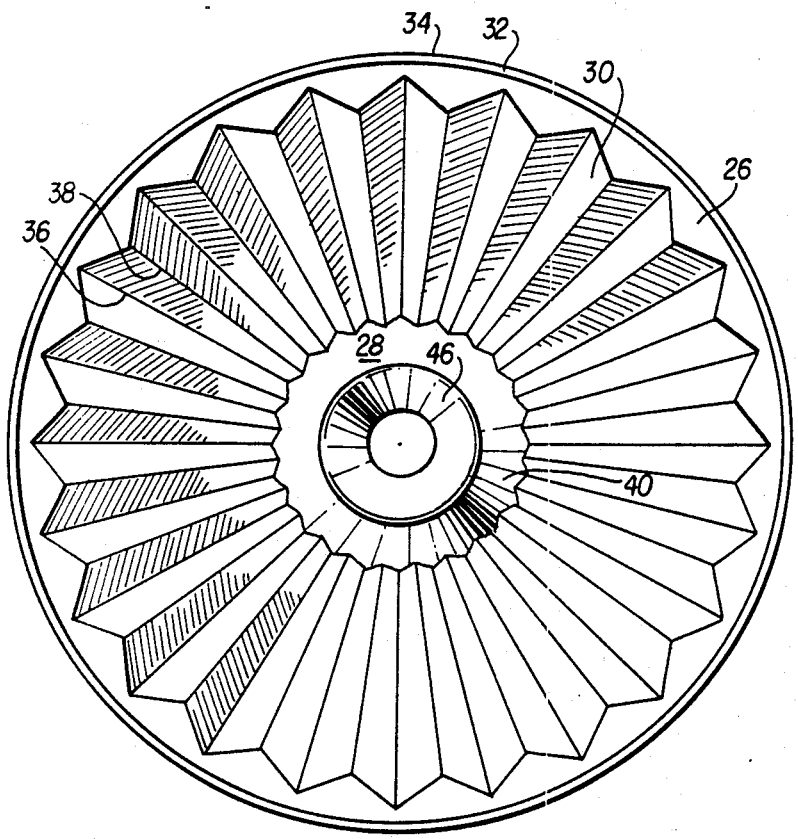
FIG. 2 is a top view of the hypodermic needle removal and disposal device of FIG. 1 with the covering cap.

A hypodermic needle removal and disposal device 10 includes a standard cylindrically-shaped, five hundred milliliter (500 ml), plastic, storage container 12 having a 3¼ inch diameter and a 3⅝ inch height. Thus, a closed sidewall 13 has an outer surface 14 of a size and shape which can be easily gripped by a normal human hand. A bottom wall 16 closes the bottom end of the elongated storage container while an open top end 18 is at the other end of the storage container. Near the open top end 18, there are spiral threads 20 on the outer surface 14 of the elongated storage container 12 which mesh with female threads of a cylindrical portion 22 of a needle-removing shield 24.

Figure 3:
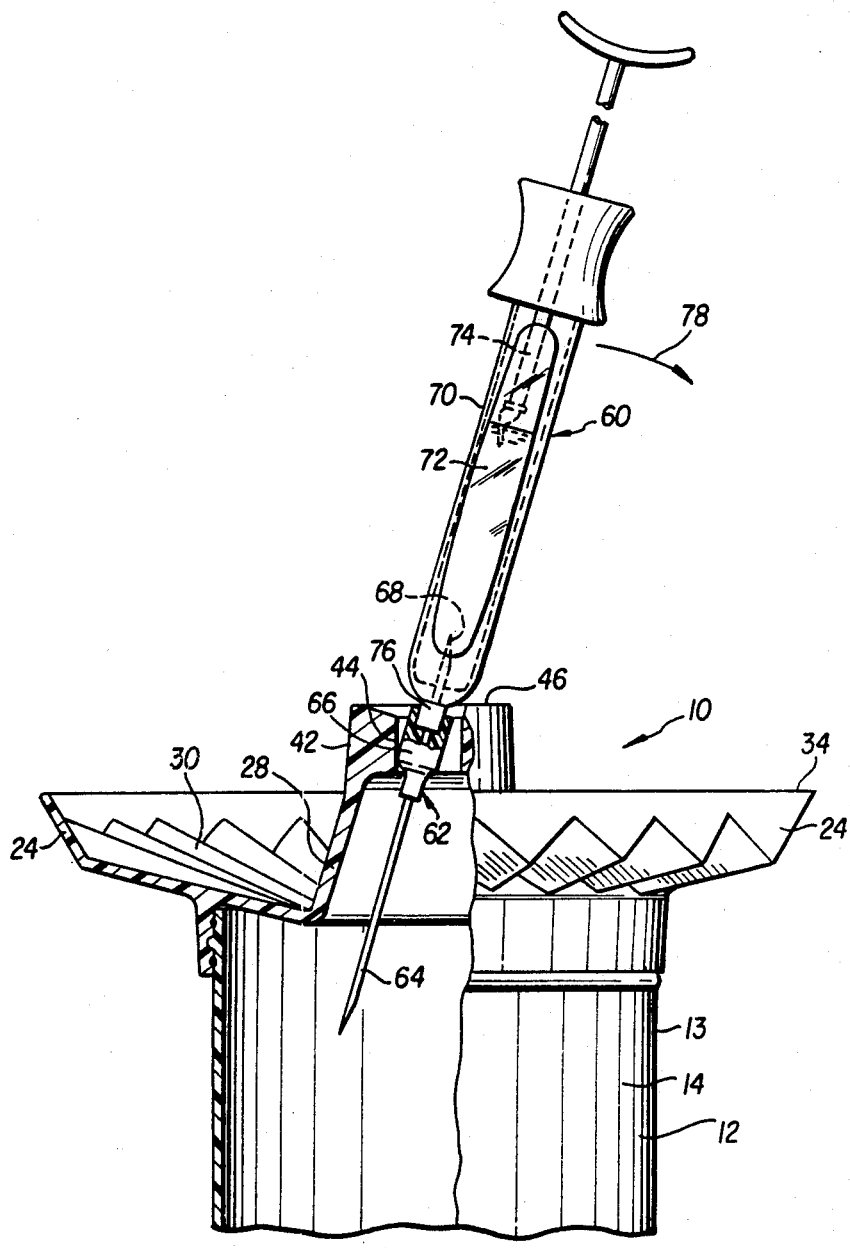
FIG. 3 is a segmented, side, partially cutaway view of the device of FIG. 1 shown removing a hypodermic needle assembly from a hypodermic syringe.

The needle-removing shield 24 comprises the cylindrical portion 22, an apron 26, and a plateau 28. The apron 26 has a funnel shaped top surface 30 directed away from the elongated storage container 12. When the elongated storage container 12 is in an upright position, as depicted in FIGS. 1 and 3, the funnel-shaped top surface 30 slopes downwardly toward the plateau 28 so that if one shoves a needle tip toward the funnel-shaped top surface 30, and the needle tip strikes the same, it will be guided toward the plateau 28 where it will come to rest. It should be noted that an outer periphery 32 of the apron 26 extends well beyond the outer surface 14 of the elongated storage container 12 to a sharp outer edge 34. In fact, in a preferred embodiment, the apron 26 extends 1⅛ inches beyond the outer surface 14. It is thought that for proper operation of the invention the apron 26 must extend at least ½ inch beyond the outer surface 14. The funnel shaped surface 30 also includes radially directed ridges 36 and troughs 38. Any needles contacting the funnel-shaped top surface 30 would be caught in the troughs 38 to be guided toward the plateau 28. The base 40 of the plateau 28 is cone shaped to provide rigid support for the plateau 28 while a top end portion 42 is reinforced by thickened walls to form an elongated hole 44 extending downwardly from a plateau surface 46. The plateau surface 46 is also funnel shaped to guide any needle tip contacting it into the elongated hole 44 and to seal with a covering cap 50 described below for preventing the escape of needles. In the preferred embodiment, the elongated hole 44 is circular, having a diameter of approximately ⅜ inch and an axial length of ⅜ inches. As can be seen in FIG. 1, the funnel shaped plateau surface 46 is positioned approximately 1½ inches above the bottom of its base 40 and approximately ⅜ inches above the sharp outer edge 34.

Although the needle-removing shield 24 is screwed onto the elongated storage container 12, it is also secured thereto by three rachet-type fasteners 47 placed in a symmetrical fashion about the circumference of the cylindrical portion 22 of the needle removing shield 24. The fasteners are placed in a manner such that they pass through the cylinder portion 22 and the spiral threads 20 of the elongated storage container 12. Once placed, the ratchet fasteners are permanent and cannot be removed without destroying the fastener or the container. In addition, it is also possible to weld the cylindrical portion 22 to the elongated storage container 12 at 48 so that these two members cannot be removed from one another, although this welding is usually unnecessary. Thus, the needle-removing shield 24 is permanently mounted on the elongated storage container 12.

The separate covering cap 50, which is specifically designed to prevent a contained needle from escaping or projecting out the top of the elongated storage container 12, has a central pedestal 52 with four outwardly directed barbs 54 near a bottom end thereof. The pedestal 52 can be forced into the elongated hole 44, but once the barbs 54 thereof extend beyond a shoulder 56 at the bottom of reinforcing forming the elongated hole 44 they impinge on a bottom surface of the shoulder so that they do not allow the covering cap 50 to be removed from the needle-removing shield 24. A particular feature of the covering cap 50 is that it has weep hole slots 58 for preventing sealing contact with the plateau surface 46 and the wall forming the elongated hole 44 to allow ventilation between an interior of the elongated storage container 12 and outside atmosphere. These weep-hole slots 58 allow expansion of gases in the elongated storage container 12 when the container is autoclaved so that there is no danger of the hypodermic needle removal and disposal device 10 exploding during sterilization thereof. The funnel shape of the plateau surface 46 first contacts an outer periphery of a head of the covering cap 50 but allows a center of the head, and the attached pedestal 52, to be resiliently pressed downwardly to cause the barbs 54 to engage the shoulders 56. Thus, the funnel shape of the plateau surface 46 reduces the necessity for exact tolerances while allowing tight sealing of the covering cap 50 on the surface 46 for preventing the escape of needles.

Describing use of the hypodermic needle removal and disposal device 10, with reference mainly to FIG. 3, the device is constructed by molding the elongated storage container 12 and the needle-removing shield 24 separately of a hard plastic such as a polypropylene or the like. Thereafter, these two members are screwed together and the ratchet type fasteners 47 are applied thereto. This composite device, including the covering cap 50, is then sold with the covering cap 50 not mounted thereon.

One uses the hypodermic needle removal and disposal device 10 as is depicted in FIG. 3 by manipulating a hypodermic syringe 60 so that most of a hypodermic needle assembly 62, including a hypodermic needle 64, a mounting hub 66, and a reverse needle 68, extend down through the elongated hole 44. Most mounting hubs 66 of hypodermic needle assemblies 62 have a diameter of approximately 5/16, which is approximately 1/16 less than the ⅜ inch diameter of the elongated hole 44, thus, the mounting hub 66 will easily extend down through the elongated hole 44, however, there will not be a great deal of room on the side thereof. It should be noted that the hypodermic syringe 60 depicted in FIG. 3 is of a type that is used by many dentists. That is, it is comprised of a stainless steel metal frame 70 having a glass vial 72 mounted therein with a membrane which is punctured by the reverse needle 68 and from which an anesthetic is forced by a plunger 74. The metal frame 70 includes a nozzle 76 having male threads on the outer surface thereof which cut female threads in the plastic mounting hub 66 of the hypodermic needle assembly 62. In any event, once the hypodermic needle assembly 62, is fully extended into the elongated hole 44, the hypodermic syringe 60 is rotated laterally in a direction depicted in FIG. 3 by arrow 78. Thus, the hypodermic syringe 60 rotates at the mounting hub 66; however, the mounting hub 66 itself is prevented from rotating by the reinforced top end portion 42 of the plateau 28 which defines the elongated hole 44. The mounting hub 66, therefore, deforms, allowing the male threads on the nozzle 76 to pull away from self tapped female threads in the mounting hub 66. Eventually, the nozzle 76 is completely outside of the mounting hub 66 and the needle assembly 62 falls into the elongated storage container 12.

It should be appreciated, that this is accomplished by a medical person using one hand to hold the elongated storage container 12 and the other hand to manipulate the hypodermic syringe 60. In this respect, it will be appreciated by those of ordinary skill in the art that when the medical operator awkwardly manipulates either or both of his or her hands to place the hypodermic needle 64 into the elongated hole 44, there is virtually no chance of sticking him or herself. That is, should the medical operator fail to place the hypodermic needle 64 in the elongated hole 44, but rather cause the needle to strike the funnel shaped plateau surface 46, the hypodermic needle will be guided into the hole 44. On the other hand, if the operator completely misses the plateau 28, the needle will be caught by the funnel-shaped top surface 30 of the needle-removing shield 24 and guided to the plateau 28. The ridges and troughs 36 and 38 of the funnel-shaped surface 30 will ensure that the needle is guided to the plateau 28. Finally, if the medical operator completely misses the hypodermic needle removal and disposal device, he or she will not bring the needle 64 in contact with his or her hand holding the elongated storage container 12, because this hand is protected by the approximately 1 inch overhang of the needle-removing shield 24.

It will also be appreciated by those of ordinary skill in the art that by substantially raising the funnel shaped plateau surface 46 above the sharp outer edge 34 of the needle-removing shield 24 an operator is allowed to rotate the hypodermic syringe 60 to a greater extent about the mounting hub 66 for causing release of the nozzle 76 from the mounting hub 66. That is, the hypodermic syringe 60 will not be obstructed from lateral rotation by the needle-removing shield 24 until it has been rotated below the plateau surface 46 outside the plateau 28.

While the invention has been particularly shown and described with reference to a preferred embodiment, it will be understood by those skilled in the art that various changes in form and detail may be made therein without departing from the spirit and scope of the invention. For example, the plateau 28 could be supported and reinforced in various ways. Further, the elongated hole 44 could be longer than a ⅜ inch size given for the preferred embodiment. Also, the needle removing shield 24 could be fastened to the elongated storage container 12 in various ways.

The embodiments of the invention in which an exclusive property or privilege are claimed are defined as follows:

1. A hypodermic needle removal and disposal device for detaching hypodermic needle assemblies, including needles and hubs, from hypodermic syringes, said device comprising:
   an elongated storage container having closed side and bottom walls and an open top, the side wall of said storage container having an outer surface of a size and shape that it can be gripped by a single normal-size human hand and held in an upright attitude;
   a needle-removing shield permanently mounted at the top of said elongated storage container for closing said open top, said needle-removing shield comprising an apron extending laterally outwardly substantially beyond the outer surface of said side wall, said apron having a funnel-shaped top surface facing away from said storage container, said funnel-shaped top surface slanting toward a plateau, said plateau rising over the funnel shaped top surface to form a plateau surface above said funnel-shaped top surface and defining an elongated hole in said plateau surface of a relatively uniform dimension along the length thereof and being of a size for closely receiving a hub of a hypodermic needle;
   whereby a hypodermic needle mounted on threads of a hypodermic syringe can be inserted through said elongated hole, so that said hub of said hypodermic needle is positioned in said elongated hole, said hypodermic syringe can be turned as a lever about said hypodermic needle hub, which is held from turning by a wall defining said elongated hole, thereby ripping threads of said syringe out of engagement with said hub and allowing said hypodermic needle to fall into said elongated storage container, said funnel shaped top surface serving as a shield for a hand holding said elongated container and guiding needles contacting it toward said plateau.

2. A hypodermic needle removal and disposal device as in claim 1, wherein said wall of said plateau defining said elongated hole is reinforced to be thicker than walls forming the remainder of said needle-removing shield.

3. A hypodermic needle removal and disposal device as in claim 2, wherein said apron includes an outer periphery thereof defining a relatively sharp outer edge such that said funnel-shaped top surface extends approximately to said sharp outer edge.

4. A hypodermic needle removal and disposal device as in claim 2, wherein said funnel-shaped top surface has radially directed troughs therein for guiding points of needles toward said plateau.

5. A hypodermic needle removal and disposal device as in claim 1, wherein said funnel-shaped top surface has radially directed troughs therein for guiding points of needles toward said plateau.

6. A hypodermic needle removal and disposal device as in claim 5, wherein said apron includes an outer periphery thereof defining a relatively sharp outer edge such that said funnel-shaped top surface extends approximately to said sharp outer edge.

7. A hypodermic needle removal and disposal device as in claim 6, wherein is further included a covering cap for preventing disposed needles from extending beyond said covering cap, said covering cap having a pedestal thereon to be inserted through said elongated hole, said pedestal having barbs at a bottom end thereof for snagging said wall forming said elongated hole to thereby prevent said covering cap from being removed from said elongated hole.

8. A hypodermic needle removal and disposal device as in claim 7, wherein said covering cap includes weep holes therethrough for allowing release of pressure from the interior of said elongated storage container.

9. A hypodermic needle removal and disposal device for detaching hypodermic needle assemblies, including needles and hubs, from hypodermic syringes, said device comprising:
   an elongated storage container having closed side and bottom walls and an open top, the side wall of said storage container having an outer surface of a size and shape that it can be gripped by a single normal-size human hand and held in an upright attitude;
   a needle-removing shield permanently mounted at the top of said elongated storage container for closing said open top, said needle-removing shield comprising an apron extending laterally outwardly substantially beyond the outer surface of said side wall, said apron having a top surface facing away from said storage container, a plateau rising over said top surface to form a plateau surface above said top surface and defining an elongated hole in said plateau surface of a relatively uniform dimension along the length thereof and being of a size for closely receiving a hub of a hypodermic needle;
   whereby a hypodermic needle mounted on threads of a hypodermic syringe can be inserted through said elongated hole, so that said hub of said hypodermic needle is positioned in said elongated hole, said hypodermic syringe can be turned as a lever about said hypodermic needle hub, which is held from turning by a wall defining said elongated hole, thereby ripping threads of said syringe out of engagement with said hub and allowing said hypodermic needle to fall into said elongated storage container, said needle-removing shield serving as a shield for a hand holding said elongated container.

10. A hypodermic needle removal and disposal device as in claim 9, wherein is further included a covering cap having a pedestal thereon to be inserted through said elongated hole, said pedestal having barbs at a bottom end thereof for snagging said wall forming said elongated hole to thereby prevent said covering cap from being removed from said elongated hole.

11. A hypodermic needle removal and disposal device as in claim 9, wherein a radially outwardly directed surface of said plateau as the shape of a truncated cone.

* * * * *